United States Patent [19]

Flesher et al.

[11] Patent Number: 4,773,984

[45] Date of Patent: Sep. 27, 1988

[54] VERTICAL GEL SLAB ELECTROPHORESIS APPARATUS

[75] Inventors: Robert W. Flesher, Baltimore; Kevin J. Barnes, Frederick; Robert W. Lynn, Germantown; Robert W. Blakesley, Frederick, all of Md.

[73] Assignee: Life Technologies, Inc., Gaithersburg, Md.

[21] Appl. No.: 9,708

[22] Filed: Feb. 2, 1987

[51] Int. Cl.$^4$ .................. G01N 27/28; G01N 27/26

[52] U.S. Cl. ........................... 204/299 R; 204/182.8

[58] Field of Search ............ 204/299 R, 182.8, 182.9; 269/91, 152, 243; 403/373, 338; 248/509, 451, 452; 24/525, 569

[56] References Cited

U.S. PATENT DOCUMENTS

| | | | |
|---|---|---|---|
| 3,129,158 | 4/1964 | Raymond et al. | 204/299 R |
| 3,222,053 | 12/1965 | Severdia | 269/91 |
| 3,677,930 | 7/1972 | Meshbane et al. | 204/299 |
| 3,819,505 | 6/1974 | Parent et al. | 204/299 |
| 3,847,773 | 11/1974 | Snyder | 204/299 R X |
| 3,932,265 | 1/1976 | Hoefer | 204/299 R |
| 3,969,218 | 7/1976 | Scott | 204/299 R |
| 3,989,612 | 11/1976 | Kragt et al. | 204/299 R X |
| 4,035,377 | 7/1977 | Detroy | 204/299 R X |
| 4,049,534 | 9/1977 | Posner | 204/299 R X |
| 4,061,560 | 12/1977 | Hannig et al. | 204/299 R |
| 4,061,561 | 12/1977 | Fletcher et al. | 204/299 R |
| 4,123,346 | 10/1978 | Ploix | 204/299 R |
| 4,124,470 | 11/1978 | Dahms | 204/299 R X |
| 4,142,960 | 3/1979 | Hahn et al. | 204/299 R |
| 4,151,065 | 4/1979 | Kaplan et al. | 204/299 R |
| 4,154,669 | 5/1979 | Goetz | 204/299 R |
| 4,187,160 | 2/1980 | Zimmermann | 204/299 R X |
| 4,190,510 | 2/1980 | Larbig | 204/185 |
| 4,194,963 | 3/1980 | Denckla | 204/299 R |
| 4,218,302 | 8/1980 | Dalisa et al. | 204/299 R |
| 4,234,400 | 11/1980 | Kaplan et al. | 204/299 R X |
| 4,284,491 | 8/1981 | Vesterberg | 204/299 R |
| 4,289,596 | 9/1981 | Satoh | 204/299 R |
| 4,292,161 | 9/1981 | Hoefer et al. | 204/182.8 |
| 4,323,439 | 4/1982 | O'Farrell | 204/299 R X |
| 4,325,796 | 4/1982 | Hoefer et al. | 204/299 R X |
| 4,337,131 | 6/1982 | Vesterberg | 204/299 R X |
| 4,358,358 | 11/1982 | Rhodes | 204/299 R |
| 4,374,723 | 2/1983 | Vesterberg | 204/299 R |
| 4,383,905 | 5/1983 | Richman | 204/299 R X |
| 4,415,418 | 11/1983 | Turre et al. | 204/180 G |
| 4,545,878 | 10/1985 | Bridges | 204/157.1 R |
| 4,574,040 | 3/1986 | Delony et al. | 204/299 R |
| 4,576,693 | 3/1986 | Kreisher et al. | 204/299 R X |
| 4,576,702 | 3/1986 | Peck et al. | 204/299 R |
| 4,576,703 | 3/1986 | Peck et al. | 204/299 R |
| 4,588,491 | 5/1986 | Kreisher et al. | 204/299 R |
| 4,618,408 | 10/1986 | Malavarca et al. | 204/299 R |
| 4,622,123 | 11/1986 | Nejame, Jr. | 204/299 R |
| 4,624,768 | 11/1986 | Yoshida et al. | 204/299 R |
| 4,657,655 | 4/1987 | Smoot et al. | 204/299 R |

OTHER PUBLICATIONS

McDonell, "Analysis of Restriction Fragments of T7 DNA and Determination of Molecular Weights by Electrophoresis in Neutral and Alkaline Gels", Jnl Mol. Biol. 110. pp. 119–146.

"The Astec Band-It" (advertisement).

"Apparatus for Sequencing" (Model STS-45) (advertisement).

"Macrophor System" (advertisement).

"New Sequi–Gen (TM) Nucleic Acid Sequencing System" (advertisement).

"Poker Face (R) Nucleic Acid Sequencer" (advertisement).

"Hoefer Scientific Instruments", catalog, pp. 26–33. [(c) 1983 handwritten].

*Primary Examiner*—John F. Niebling
*Assistant Examiner*—John S. Starsiak, Jr.
*Attorney, Agent, or Firm*—Saidman, Sterne, Kessler & Goldstein

[57] ABSTRACT

A vertical gel slab electrophoresis apparatus is disclosed comprised of a vertically oriented gel slab arranged between upper and lower buffer solution reservoirs. A bifurcated movable tray contains both an upper buffer reservoir drain and lower buffer reservoir. Both upper and lower buffer reservoirs are provided with hinged covers which act as electrical interlocks to prevent unsafe operation of the apparatus, as well as prevent spillage of buffer solution. The design overcomes safety problems associated with both electrical shock and radioactive chemical contamination. The apparatus is provided with handles for each relocation. Cooling vents are provided for ambient air cooling of the apparatus. A gel mold experiment can be assembled and disassembled with unusual ease with the aid of unique self-locking clamp assemblies.

36 Claims, 6 Drawing Sheets

VERTICAL GEL SLAB ELECTROPHORESIS APPARATUS

BACKGROUND OF THE INVENTION

1. Field of the Invention

The present invention relates generally to apparatus for performing electrophoresis, and in particular, to an apparatus in which gel slabs are supported on a gel slab platform in the vertical position in conjunction with the necessary buffer solutions for the electrophoretic separation of samples.

2. Related Art

Numerous electrophoresis devices have been developed since the discovery that charged particles suspended between opposite poles and in an electric field migrate toward the pole possessing the charge opposite that the particle. The extent of migration is an indication of the composition of the particles.

Many apparatus have been designed to facilitate gel electrophoresis of biologically significant macromolecules. Some apparatus are designed so as to orient the gel vertically; others are designed to orient the gel horizontally. A vertical orientation has been generally found to be preferred for the electrophoresis of nuclei acids in such applications as nucleic acid sequencing.

Apparatus designed to facilitate the electrophoretic separation of DNA or RNA fragments generated as part of nucleic acid sequencing procedures share a number of elements. These common elements include; a gel slab composed of two flat glass plates separated by thin strips placed at opposite edges and between these plates enclosing a gel composed of polyacrylamide cast between the plates within which the electrophoretic separation will be carried out; a vertically oriented support platform to which the gel slab can be secured; means for securing the gel slab to the support platform; two reservoirs for containing buffer, one installed toward the upper end of the vertical slab support and a second installed toward the lower end of the vertical slab support; and an electrode installed in each reservoir to apply a voltage to buffer added to the reservoir. Placement of the gel slab against the vertical platform situates the gel so that when buffer is added to each of the reservoirs and an effective electrical contact is established between the buffer in one reservoir and the buffer in the other reservoir through the gel to be used to electrophoretically separate the components of the test samples. Owing to the geometry of this assembly, most of the voltage difference between the electrodes occurs within the gel.

The usual practice of electrophoresis as applied to nucleic acid sequencing requires an apparatus constructed to hold a gel slab typically measuring from 200 to 400 inches square (one dimension is usually no larger than 4 times the other dimension). Gel slabs of this size require the use of heavy gauge glass plates. Further, when electrophoretic separation is carried out substantial heat is generated in the gel slab. This heat is conveniently removed by placing a large conducting plate in contact with the gel slab, most conveniently, by incorporating this plate as part of the vertical platform against which the gel slab is placed. Consequently such apparatus tend to be heavy and difficult to carry. As a practical matter electrophoresis of this type require the application of high voltages between the buffer reservoirs; voltages which present a danger of accidental electrocution, to users of the apparatus. As a further practical matter most nucleic acid sequencing procedures require the addition of hazardous quantities of radioactive materials to the gel and the subsequent contamination of the buffer contained in the reservoirs, particularly the buffer in the lower reservoir, with radioactive material. All these considerations make convenience, transportability, ease of cleaning, and safety important to users of this type of apparatus.

SUMMARY OF THE INVENTION

The various novel elements embodied in the present invention separately and together provide for an apparatus for gel electrophoresis which is substantially safer and more useful than conventional apparatus. While the elements of the present invention are particularly valuable as applied to apparatus designed specifically for electrophoresis of gels used in nucleic acid sequencing, they may also be profitably applied to apparatus intended for other applications.

The present invention features novel provision in a vertical gel slab electrophoresis apparatus which overcomes the problems and deficiencies found in conventional devices.

It is a feature of the present invention to provide a vertical electrophoresis apparatus wherein the required buffer solutions are kept segregated at all times. Segregation is accomplished by the creation and usage of a novel bifurcated removable tray located within the lower buffer solution containment area.

The present invention also provides a novel easily operated upper buffer solution drain assembly which can operate in conjunction with the above noted bifurcated tray allowing for safe and easy disposal of hazardous buffer solutions. Further, the unique overall shape and design of the vertical gel slab electrophoresis apparatus is extremely stable and compact due to a very low center of gravity. The unique shape of the preferred embodiment of the present invention also lends itself to placement of handle points on both vertical sides of said apparatus for ease of movement of the entire apparatus from one location to another.

The preferred embodiment of the present invention also contemplates novel self-locking continuously adjustable attachment mechanisms. These self-locking mechanisms operate without the unwieldy springs or clips as used in conventional devices for the retention and clamping of the gel mold plates to the upright gel platform. The self-locking attachment mechanisms of the present invention are simple and easy to use, and better control the compression exerted on the gel mold.

Another feature of the present invention is the novel electrical interlock assemblies that prevent electrical shock and provide for easy application of electrical potential to the separate electrical poles within the apparatus. Such provision could take the form of unique hinged covers movably attached over both upper and lower buffer reservoirs in the present invention. Each said cover is hinged to the vertical supports of the apparatus. An opening in each said cover and the vertical supports provides for easy insertion of a standard rigid electrical connector, or "banana plug," therebetween in such a manner as to make secure contact with an non-corroding electrode within the respective buffer reservoir. The electrical connection may be made only if the buffer reservoir cover is closed so as to effectively obstruct access to the buffer contained on the buffer reservoir and having been thus made also prevents opening of the respective buffer reservoir cover while electrical connection is maintained. These buffer reservoir covers also serve the secondary function in the present invention of segregating said upper and lower buffer reservoirs from each other in order to prevent contamination and spillage. Further features of preferred embodiments of the present invention will be evident from the description that follows.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF THE PREFERRED EMBODIMENT

The vertical gel slab formation and electrophoresis apparatus of the present invention provides advantages and capabilities heretofore unavailable in conventional gel slab electrophoresis devices.

Figure 1:
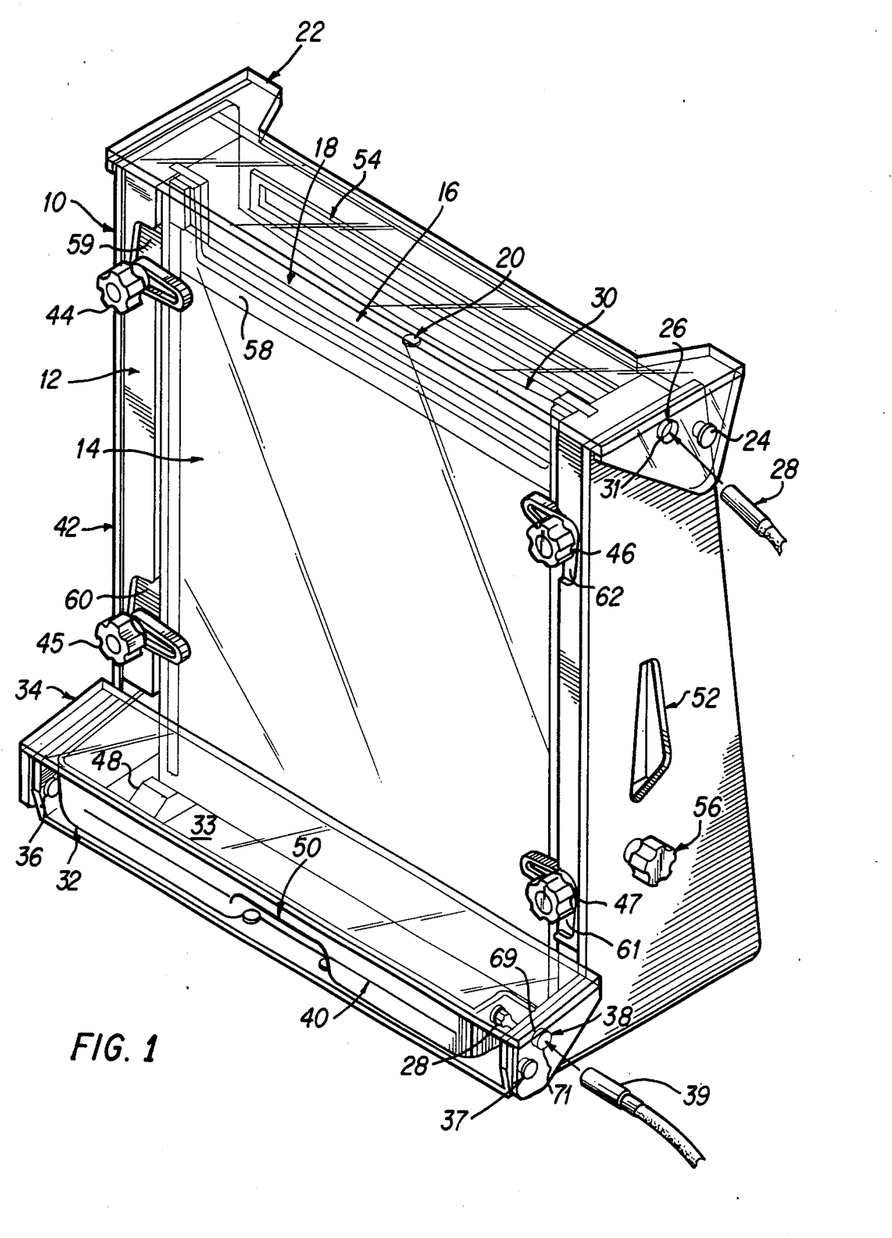
FIG. 1 is a perspective view of the preferred embodiment of the present invention in the assembled form for use in running an electrophoresis experiment.
Figure 2:
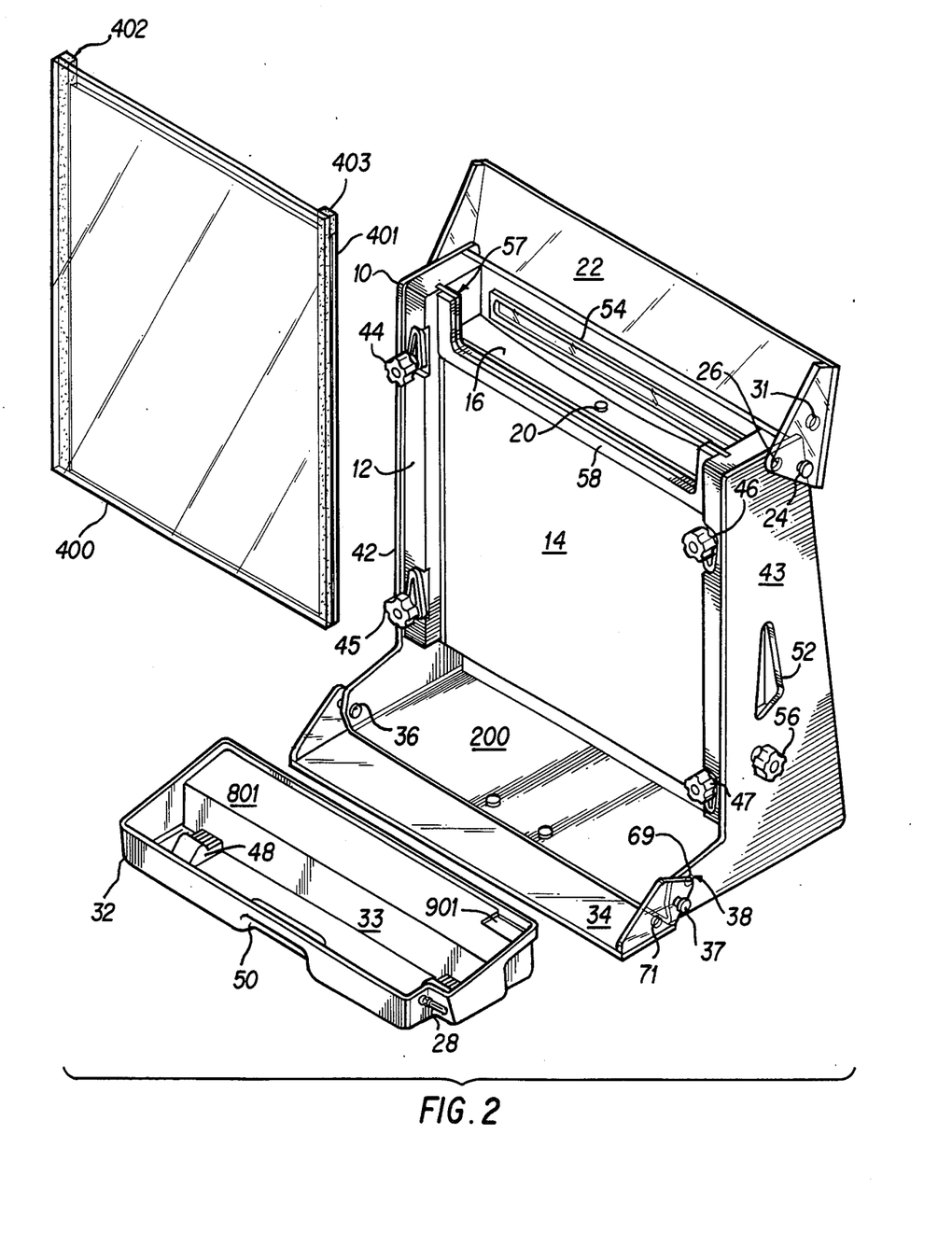
FIG. 2 is an exploded perspective view of the embodiment of FIG. 1 showing the present invention in a disassembled form with the lower buffer reservoir tray removed from its position in the frame, with the upper buffer reservoir cover and the lower buffer reservoir cover in the opened position, respectively, and with the gel mold assembly removed from the vertical gel slab platform.
Figure 6:
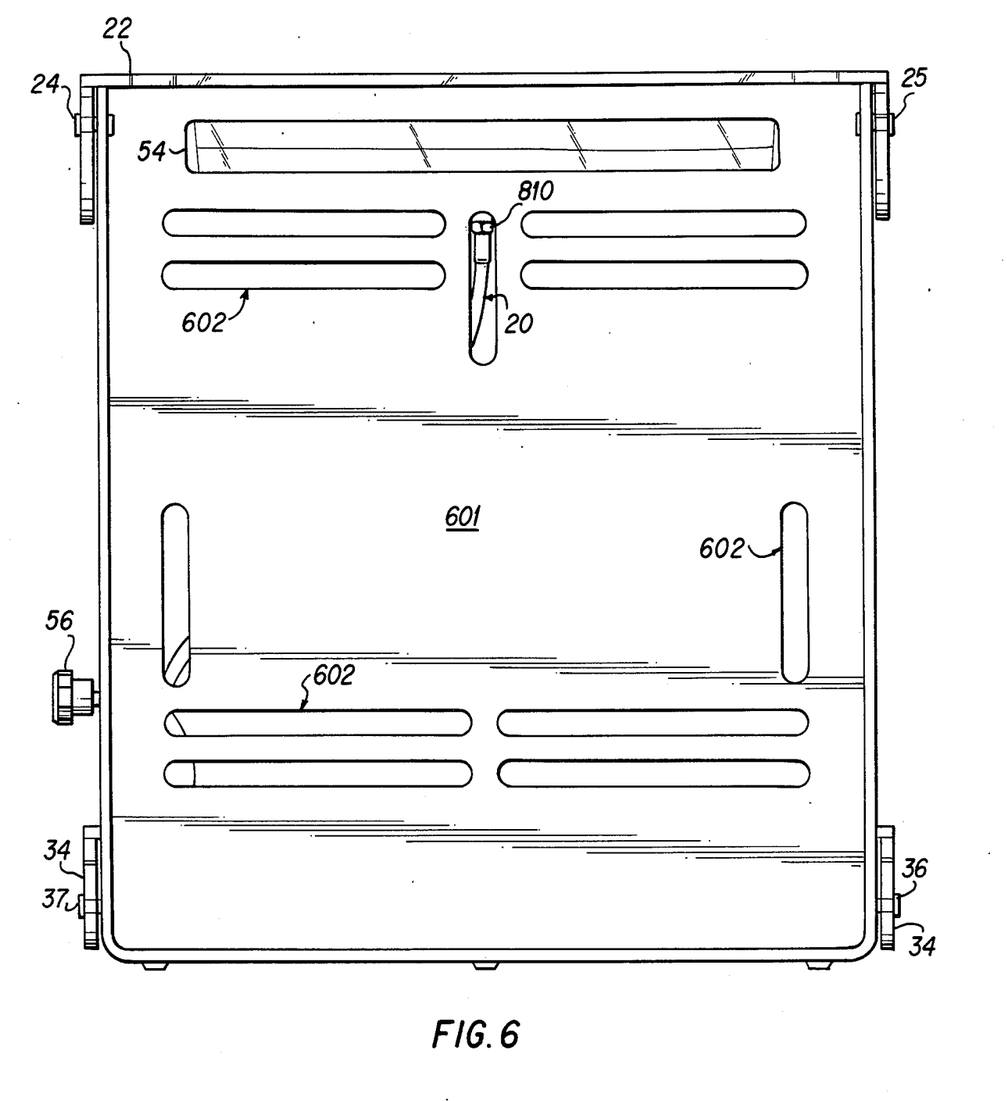
FIG. 6 is a back, plan view of the preferred embodiment of FIG. 1.

Referring first to FIGS. 1, 2, and 6, the nucleic acid sequencing electrophoresis unit of the present invention is shown having vertical left and right side partitions 42 and 43, respectively, a main front panel 12, a bottom panel 200, and a back panel 601. Main front panel 12, bottom panel 200, and back panel 601 are joined (fastened or made integral) in any conventional fashion to vertical side partitions 42 and 43 to form an upright device or frame that is unusually stable due to the low center of gravity inherent in the trapezoidal design of the vertical left and right side partitions 42 and 43.

In the preferred embodiment of the present invention, a second front panel 14 is located adjacent main front panel 12 (see FIG. 2). Second front panel 14 and main front panel 12 thereby define a vertical gel slab platform that extends upwardly to the front edge of an upper buffer reservoir 18 and downwardly to a lower buffer reservoir tray 32. A lower buffer reservoir 33 is integrally formed in lower buffer reservoir tray 32. In the preferred embodiment of the present invention, lower buffer reservoir tray 32 is placed in use between frontward projecting extensions of left and right side partitions 42 and 43 and sits on the bottom panel 200, as shown in FIG. 1. It should be noted that lower buffer reservoir tray 32 could be made integral with device 10; however, in the preferred embodiment, the tray 32 is removable from device 10.

In a typical electrophoresis experiment, heat is generated within the gel contained within the gel slab. It is desirable to efficiently dissipate this heat across the face of the present invention as defined by front panel 12. In order to effectively dissipate this heat, it is preferred that the second front panel 14 is a good thermal conductor, and may be made of a metal, although any of numerous non-metallic materials could be used. Further, usage of a non-ferrous metal lends itself to easy maintenance and long life due to lack of oxidation.

Figures 7, 8:
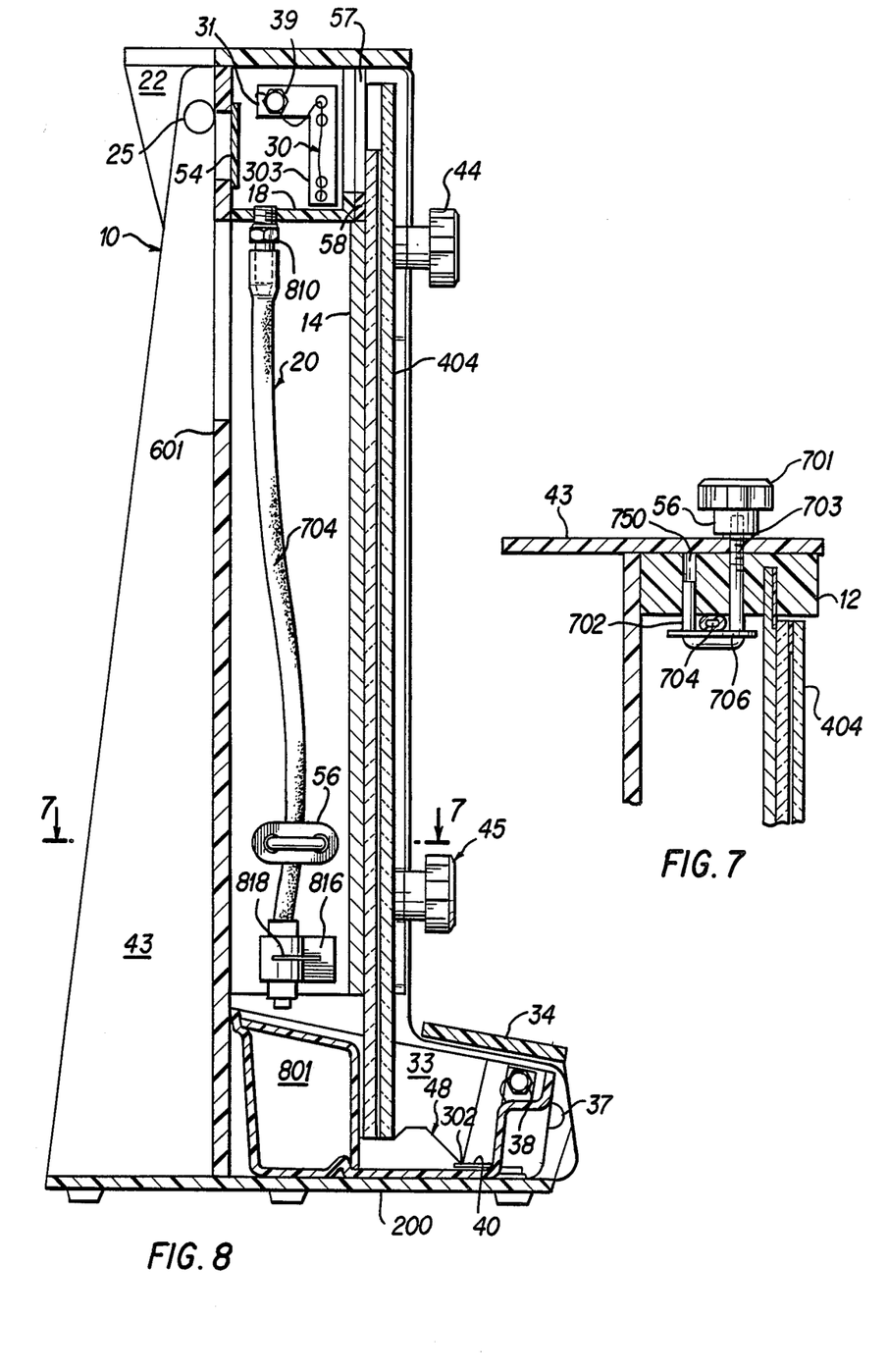
FIG. 7 is an cross-sectional view of the preferred embodiment of the petcock assembly, taken along line 7—7 of FIG. 8.
FIG. 8 is an enlarged, sectional view of the preferred embodiment of FIG. 1, taken along center line 8—8 of FIG. 6.

As seen best in FIGS. 2, 6, and 8, first or upper buffer solution reservoir 16 is defined in part by a back panel 601 having a transparent window 54, an upper buffer reservoir floor 18, a seal gasket 58, a U-shaped front piece 57, and the inside surfaces of top portions of the left and right vertical side partitions 42 and 43. As best shown in FIGS. 2 and 8, a gel mold assembly 404, in which the desired electrophoretic action occurs, is placed between the upper buffer reservoir 16 and a second or lower buffer reservoir 33. The desired electrophoretic action is caused by the application of an electrical potential (not shown) to the upper and lower buffer solutions causing an electrical differential across the gel mold 404.

In order to prevent both electrical shock and buffer solution spillage or contamination, upper buffer reservoir 16 is maintained closed or inaccessible during use by a hinged top closure panel 22. Hinged top closure panel 22 is rotatably attached to upper hinge pins 24 and 25 fastened to side partitions 42 and 43 so that panel 22 can rotate between a first or open position as shown in FIG. 2 to a second or closed position as shown in FIG. 8.

The prevention of shock to the experimenter and contamination of the buffer solution contained in the upper buffer reservoir 16 is a major aspect of the present invention. It can be appreciated that in a typical electrophoresis experiment very high electrical potentials are often used, requiring great care and awareness both by the experimenter and those individuals in the vicinity of the experiment. The present invention eliminates electrical shock hazards by provision of a restrictive electrical connection that can be attained only when the top closure panel 22 is in the closed position which obstructs access to the buffer solution in said reservoir.

Specifically, an upper electrical interlock 26 includes a banana plug 39 mounted in a recess 29 formed in the upper portion of the right side partition 43. A hole 31 in the right side panel of top closure panel 22 is positioned so that it is in alignment with recess 29 when the top closure panel 22 is in the closed position. It can be seen best from FIG. 3 that an upper electrical connector 28 can be electrically engaged with banana plug 39 only when the top closure panel is in the closed position.

Figure 3:
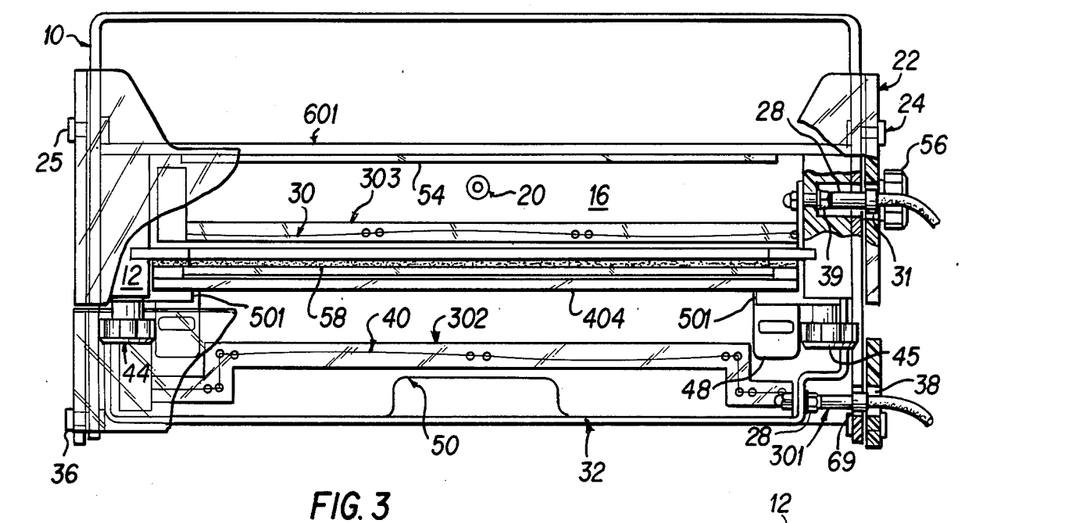
FIG. 3 is a partially broken, top view of the preferred embodiment of in FIG. 1.

The electrical connection between the upper electrical connector 28 and the banana plug 39 physically prevents the rotation of the top closure panel 22 from the closed position. Thus, the experimenter cannot be shocked by contact with the buffer solution in the upper buffer reservoir 16 since electrical power can only be applied when the top closure panel 22 is in the closed position. It should be noted in this regard that the side panel of top closure panel 22 covers the recess 29 except when the top closure panel 22 is in the closed position, thereby preventing the experimenter from defeating the electrical safety aspect of the top closure panel 22. Moreover, the top closure panel 22 in the closed position prevents contamination of the buffer solution contained in the upper buffer reservoir 16.

Figure 4:
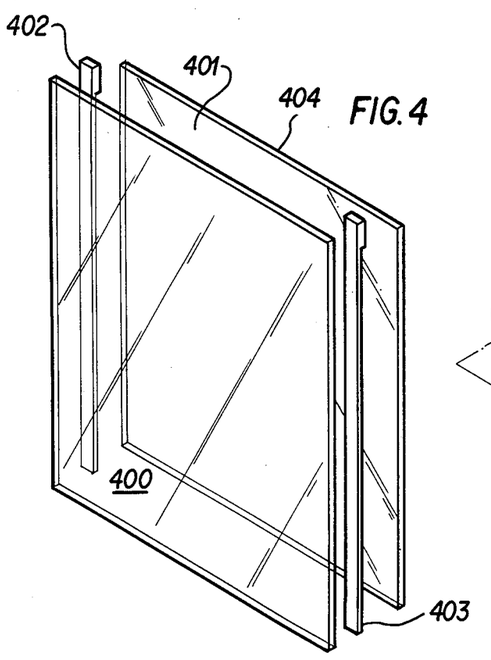
FIG. 4 is an exploded view of the gel mold assembly of the preferred embodiment of FIG. 1 showing the first glass plate, second glass plate, and spacer gaskets.

Referring now to FIGS. 3, 4, and 8, the upper buffer reservoir 16 has an upper platinum electrode 30, which is electrically attached to the banana plug 39. Upper platinum electrode 30 is looped through holes provided in an L-shaped mounting strip 303. The L-shaped mounting strip 303 acts to maintain the upper platinum electrode 30 in the desired position in the buffer solution in the upper buffer reservoir 16. It should be noted that in the preferred embodiment of the present invention platinum metal is preferred for the upper platinum electrode 30; however any noncorroding metallic element such as gold, rhodium, or palladium may be utilized as an electrode in the present invention.

As best shown in FIG. 1, and in the interest of electrical safety and preventing contamination of the buffer solution, the lower buffer reservoir tray 32 in its inserted, operating position, is held and is covered by a bottom closure panel 34 when in a first or closed position. Bottom closure panel 34 is hinged to lower hinge pins 36 and 37 mounted in the lower portion of the left and right side partitions 42, 43. A lower electrical interlock 38 is also provided. Specifically, the lower electrical interlock 38 includes a banana plug 28 mounted in a recess 69 formed in the lower portion of the right side partition 43. A hole 71 in the right side panel of the bottom closure panel 34 is positioned so that it is in alignment with recess 69 when the bottom closure panel 34 is in the closed position. As can be seen in FIGS. 1 and 3, lower electrical connector 39 can only be electrically engaged with banana plug 28 when the bottom closure panel 34 is in the closed position. This engagement prevents the opening bottom closure panel 34 while electrical potential is applied, eliminating shock hazard to the experimenter and contamination of the buffer solution.

Figure 9:
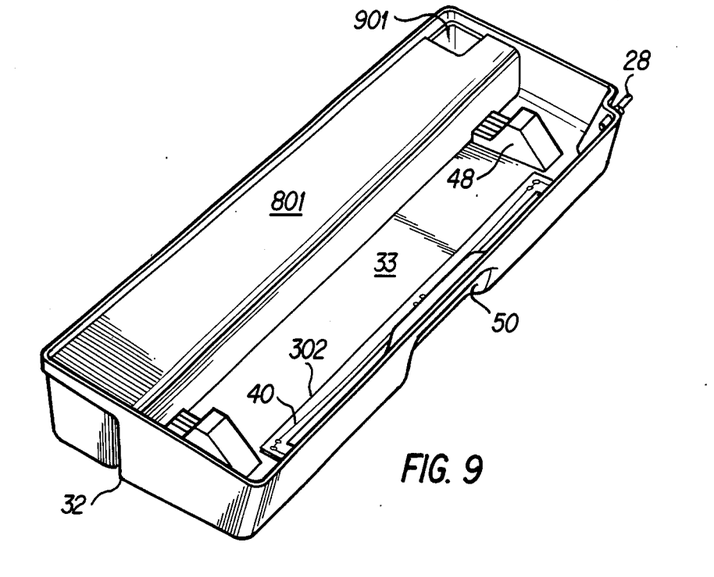
FIG. 9 is a perspective view of the lower buffer reservoir tray of the preferred embodiment of FIG. 1.

Referring now to FIGS. 3, 8, and 9, the lower buffer reservoir tray 32 has a lower platinum electrode 40, which is electrically attached to banana plug 28. Lower platinum electrode 40 is looped through holes provided in the L-shaped mounting strip 302. The L-shaped mounting strip 302 acts to maintain the lower platinum electrode 40 in the desired position in the buffer solution in the lower buffer reservoir 33.

As seen in FIGS. 6, 8, and 9, another important aspect of the present invention is the ability to separately drain the upper buffer solution from the upper buffer reservoir 16 and lower buffer solution from the lower buffer reservoir 33 at the experimenter's convenience. During the course of a typical electrophoresis experiment, either or both buffer solutions may become radioactive and problems of disposal of such hazardous waste become inherent in the conventional electrophoresis device.

In many conventional electrophoresis devices, the entire unit typically must be carried to a buffer disposal area, and bodily manipulated to pour the buffer solutions out for disposal. The presence of radioactivity in one or both buffer solutions further complicates this disposal, in that in many areas of the world (and the number is growing) radioactive material disposal is stringently monitored and is costly so as to make it undesirable to combine relatively heavily contaminated materials with materials which are non or minimally radioactive. In the conventional electrophoresis devices, the upper and lower buffer solutions are often mixed during disposal, which complicates or makes impossible segregation of the respective buffer solutions.

The present invention provides for separate drainage and disposal of the upper and lower buffer solutions without moving the unit 10. Turning first to the upper buffer solution, the upper buffer reservoir 16 has an upper buffer reservoir drain assembly 20 that facilitates draining upper buffer reservoir 16. The upper buffer reservoir drain assembly 20 includes an orifice 810 thread mounted into upper buffer reservoir floor 18 midway between the left side partition 42 and the right side partition 43. A drain hose 704 is press fitted over the second end of orifice 810 so as to be in fluid communication with the upper buffer reservoir 16. Fluid flow through drain hose 704 produced by gravitational action is controlled by a petcock assembly 56, best shown in FIG. 7 and 8, is located on the right side partition 43. Petcock assembly 56 includes a knob 701 threaded onto an L-shaped drain hose clamp 702 via threads 703; the long-side of clamp 702 extending through an opening 750 in the right side partition 43. A flat plate 706 can be inserted on clamp 702 to provide more uniform squeezing action to drain hose 704.

Drain hose 704 is routed from orifice 810 through drain hose clamp 702 and flat plate 706 to a position disposed above an upper buffer reservoir drain opening 901 provided in an upper buffer reservoir drain container 801, formed as part of the lower buffer reservoir tray 32, as shown in FIGS. 8 and 9. Note that a clamp 816 and a jacket 818 disposed around drain hose 704 maintain the second end of drain hose 704 on the proper draining position above the upper buffer reservoir drain container 801. In operation, the action by an experimenter of turning knob 701 in a clockwise direction engages threads 703 causing the movement and clamping squeeze action of drain hose clamp 702 against drain hose 704. This action seals off drain hose 704 so that no upper buffer solution can flow through drain hose 704. Conversely, the opposite rotation of knob 701 reduces the clamping action, allowing the upper buffer solution to flow through drain hose 704 to the lower buffer reservoir 33. In this fashion the experimenter can drain the upper buffer solution from the upper buffer reservoir 16 at will into the segregated upper buffer reservoir drain container 801.

Figure 10:
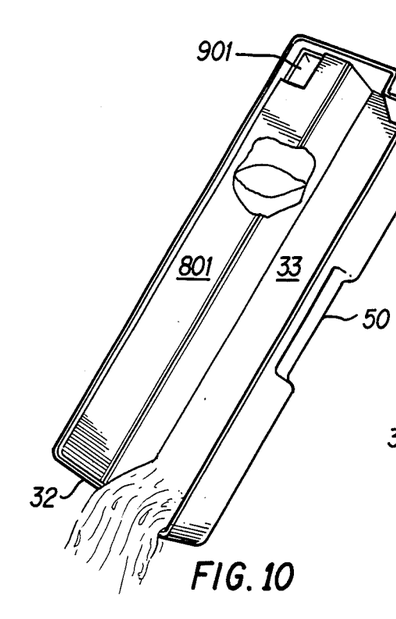
FIG. 10 is a perspective view of the lower buffer reservoir tray of FIG. 1, showing the upper buffer reservoir drain container partially cutaway and lower buffer solution emptying procedure for the lower buffer reservoir.
Figure 11:
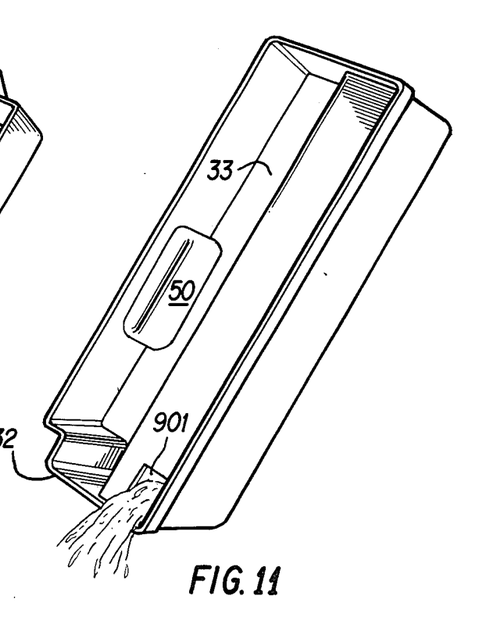
FIG. 11 is a perspective view of the lower buffer reservoir tray of FIG. 10, showing the upper buffer reservoir drain container and upper buffer solution emptying procedure via the upper buffer reservoir drain opening.

Referring additionally to FIGS. 10 and 11, the separate drainage capability for the upper and lower buffer solutions provided by the lower buffer reservoir tray 32 of the present invention can be better appreciated.

Lower buffer reservoir tray 32 includes a lower buffer reservoir tray handle 50 formed integrally into the lower buffer reservoir 33. An experimenter during the drainage operation holds the lower buffer reservoir tray 32 by handle 50. The lower reservoir tray 32 permits the separate drainage of the upper and lower buffer solutions that are being stored as follows. As shown in FIG. 10, an experimenter can pour the lower buffer solution out of the lower buffer reservoir 33 by rotating the lower buffer tray 32 to the left. Since the upper buffer reservoir drain container 801 is enclosed except for the upper buffer reservoir drain opening 901, the upper buffer solution which has been drained into the upper buffer reservoir drain container 801 is prevented from being poured out. Conversely, as shown in FIG. 11, the upper buffer solution contained in the upper buffer reservoir drain container 801 can be drained by an experimenter by rotating lower buffer reservoir tray in the opposite direction. It can be thus appreciated that the segregated drain arrangement, combined with the removable aspect of lower buffer reservoir tray 32, via lower buffer reservoir tray handle 50, allows for separate, easy, and safe disposal of either the upper buffer solution through upper buffer reservoir drain opening 901, or the lower buffer reservoir tray 32 through lower buffer reservoir 33.

The present invention, in its preferred embodiment, further eliminates yet another problem found in conventional vertical electrophoresis devices. Given a desire for vertical gel slab electrophoresis orientation, the attainment of such vertical orientation without damage to the gel mold or gel slab presents problems. For example, in a typical vertical electrophoresis experiment, an experimenter must be able to place a gel slab between the glass plates of the gel mold in a secure manner, while at the same time ensuring a three point vertical orientation of the gel mold respective to the electrophoresis device. This means that the fragile, but bulky and heavy gel mold must be held in the electrophoresis device in such a way that the uppermost edge of the gel slab intimately contacts the upper buffer solution, while the lowermost edge of the gel mold intimately contacts the lower buffer solution, and simultaneously is in a stable and secure upright and vertical position within the electrophoresis device. Conventional devices approach these issues by utilizing clips or clamps to hold the fragile glass plates of the gel mold together and secure the gel mold to the electrophoresis device. This procedure is at the very least, cumbersome and unwieldy gel mold procedures having the potential of destroying the gel mold itself. The preferred embodiment of the present invention solves these problems created by conventional devices in the following simple and efficient manner.

In the present invention, a typical gel mold set up for experimentation takes place as follows. Referring first to FIG. 4, gel mold assembly 404 comprises first glass plate 400, second glass plate 401 and spacer gaskets 402 and 403. The gel, across which electrophoretic separation takes place, is positioned between glass plates 400 and 401. Note that second glass plate 401 is vertically shorter than first glass plate 400, and that spacer gaskets 402 and 403, made of any suitable inert material, such as Teflon, are the same vertical height as first glass plate 400. As best shown in FIG. 2, the gel mold assembly, when glass plates 400 and 401 are brought together in a planar fashion with gaskets 402 and 403 therebetween, exhibits a horizontal gap the thickness of gaskets 402 and 403. It is in this gap that the gel slab resides. Also, due to the unequal height of glass plates 400 and 401, intimate contact of the uppermost end of gel mold 404 with the upper buffer reservoir 16 is attained. Referring further to FIG. 2, and additionally to FIG. 1 and 8, it can be seen that in the preferred embodiment of the present invention lower buffer reservoir 32 resides within electrophoresis unit 10 on bottom panel 200. Gel mold assembly 404 is first placed into electrophoresis unit 10 by being positioned vertically on vertical restraints 48 and 49 within lower buffer reservoir tray 32, positioned upon bottom panel 200. Gel mold assembly 404 is then positioned in a contacting relationship with second front panel 14 as shown in FIGS. 1, 4, and 8, once self locking clamp assemblies 44, 45, 46, and 47 are in the open position, as shown in FIG. 2. Thereafter, as shown in FIGS. 1 and 3, self locking clamps 44 through 47 are manipulated into the closed position, over gel mold assembly 404, hence securing gel mold assembly 404 against seal gasket 58, heat dissipating second front panel 14, and between upper buffer reservoir 16 and lower buffer reservoir 33.

Figure 5:
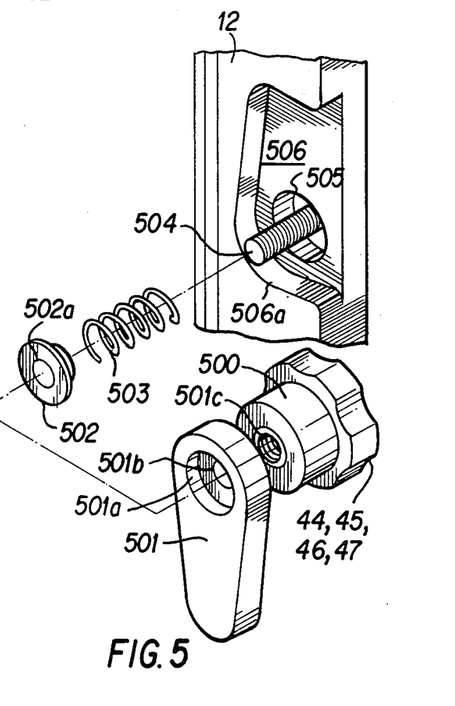
FIG. 5 is an exploded view of a self-locking clamp assembly of the preferred embodiment of FIG. 1.

It can be appreciated that self locking clamp assemblies 44 through 47, which are identically comprised, are an important aspect and provision of the present invention. FIG. 5 illustrates the subparts of a self locking claim assembly. It should be noted that said self locking clamps need not be restricted to vertical electrophoresis apparatus, said clamps exhibiting qualities such that use could be found apart from electrophoresis experimentation.

Each self locking clamp assembly operates in such a manner that with a simple twist of knob 500, clamping finger 501 swings out, over, and against gel mold assembly 404 when securing said gel mold assembly into the electrophoresis unit 10, and with a simple twist in the opposite direction as above, clamping finger 501 swings out and away from said gel mold assembly, thereby releasing it from said electrophoresis unit. It should be noted that mounting a typical gel slab assembly to the electrophoresis unit, a difficult manual operation in conventional devices, is made easy in the present invention with greatly reduced risk of mishap, by the simple one step operation of the self-locking clamps. Said clamps can be operated with one hand, of an experimenter, the experimenter's other hand being used to hold the gel mold assembly in place within the gel slab platform of the present invention.

A representative clamp assembly is comprised of threaded post 504 projecting from hole 505 and through front panel 12, recess 506 and said front panel. Situated upon said post 504 is spring 503, and finger washer 502 through washer hole 502a, clamping finger 501 through finger recess 501a and finger hole 501b. As can clearly be seen from FIG. 5, clamping finger 501 may advantageously be shaped substantially rectangularly, with rounded corners. Once all said subparts are positioned on threaded post 504, knob 500 is threaded onto said post by matingly engaging threaded hole 501c via the corresponding threads on the post 504.

It should be noted that sloping edge 506a of recess 506a in main front panel 12 corresponds in shape and size with second curve surface 506c of clamping finger 501. This allows recess 506 to serve as a resting stop for clamping finger 501, resulting in further economy of movement and ease of operation of the self locking clamp assembly.

Turning now to FIG. 6, further features of the present invention are shown. It is well known by those of skill in the art that large amounts of heat are normally dissipated across the a typical gel mold assembly of conventional electrophoresis apparatus during the electrophoretic separation of samples in a typical experiment. Such heat can lead to the destruction of the experiment due to damage to the gel mold, or breakage of the glass plates themselves. Inefficient heat dissipation also leads to the generation and maintenance of a thermal gradient within the gel of sufficient magnitude as to result in significantly different electrophoretic performance in different regions of the gel mold. This thermal gradient in conventional apparatus results in faster migration of in particular molecular species in the central region of the gel mold, the so-called "Smile Effect." As best shown in FIG. 2, the present invention solves this problem by the provision of a metallic heat conducting front panel, second front panel 14. The provision of numerous cooling vents 602 within the back panel 601, shown in FIG. 6, further eliminates heat destruction by allowing ambient air cooling of the gel mold assembly 404.

Yet another problem in the conventional electrophoresis device is the unstable and often unwieldy carrying and removal for the electrophoresis device from place to place. Referring again to FIGS. 1, 2, and 6, the provision of strategically located carrying handles, side handles 52 provide easy access to electrophoresis unit 10 and safe removal of said unit without damage to gel mold assembly 404, or affecting upper buffer reservoir 16 or lower buffer reservoir 33. As can clearly be seen from FIGS. 1 and 2, the side handles 52 may advantageously be provided in the frame as a hole in, for example, a vertical side partition such as side partition 43.

The foregoing description is intended primarily for purposes of illustration. This invention may be embodied in other forms or carried out in other ways without departing from the spirit or scope of the invention. The present embodiment is therefore to be considered in all respects a lesser to and not restricted to the particular structure or operational features described above. Modifications and variations still falling within the spirit or the scope of the invention will be readily apparent to those skilled in the art.

What is claimed is:

1. A vertical electrophoresis apparatus adapted for use with an electrical source, which apparatus comprises:
   a. an electrophoresis mold defining a region shaped to contain a gel slab;
   b. a frame supporting said electrophoresis mold for maintaining said electrophoresis mold in a substantially vertical position;
   c. a first buffer reservoir located adjacent a top of said electrophoresis mold, adapted to maintain a first buffer solution in effective electrical contact with an uppermost end of said gel slab contained in said electrophoresis mold;
   d. a second buffer reservoir located adjacent a bottom of said electrophoresis mold, adapted to maintain a second buffer solution in effective electrical contact with a lowermost end of said gel slab contained in said electrophoresis mold;
   e. first means adapted to electrically connect said first buffer solution contained in said first buffer reservoir and said second buffer solution contained in said second buffer reservoir for applying an electrical potential across said gel slab contained within said electrophoresis mold; and
   f. a lower buffer reservoir tray having a lower buffer reservoir and an upper buffer reservoir drain container, said tray disposed in said frame, said lower buffer reservoir acting as said second buffer reservoir, and said upper buffer reservoir drain container adapted to receive said first buffer solution through a drainage pathway connecting said first buffer reservoir and said upper buffer reservoir drain container.

2. The apparatus of claim 1, wherein said lower buffer reservoir tray is removable from said frame.

3. The apparatus of claim 1, wherein said upper buffer reservoir drain container of said lower buffer reservoir tray is closed except for an upper buffer reservoir drain opening.

4. The apparatus of claim 1, wherein said upper buffer reservoir drain container comprises an opening which is disposed substantially adjacent a first end of said lower buffer reservoir tray, whereby said second buffer solution in said lower buffer reservoir can be poured out of said lower buffer reservoir tray at a second end without the pouring out of said first buffer solution contained in said upper buffer reservoir drain container due to the level of the surface of said first buffer solution being maintained below the level of said opening throughout the pouring of said second buffer solution.

5. The apparatus of claim 1, wherein said lower buffer reservoir tray includes a lower buffer reservoir tray handle.

6. The apparatus of claim 1, wherein said lower buffer reservoir tray includes at least one vertical restraint which physically contacts a lowermost end of said electrophoresis mold.

7. The apparatus of claim 6, wherein said vertical restraint physically contacts and accommodates said electrophoresis mold so that an uppermost end of said electrophoresis mold is positioned in said first buffer reservoir so that said first buffer solution in said first buffer reservoir may be maintained in effective electrical contact with said upper most end of said gel slab.

8. The apparatus of claim 2, wherein said lower buffer reservoir tray includes at least one vertical restraint the physically contacting and accommodating a lowermost end of said electrophoresis mold, and for preventing the removal of said lower buffer reservoir tray from said frame by contacting said electrophoresis mold's lowermost end so that it acts as a physical barrier to removal of said buffer reservoir tray.

9. The apparatus of claim 1, wherein said electrophoresis mold comprises two plates in a spaced apart, substantially parallel relationship, and two inert spacers placed between said plates to define said region.

10. The apparatus of claim 9, wherein at least one of said plates is substantially transparent.

11. The apparatus of claim 9, wherein at least one of said plates is glass or a hydrocarbon based material.

12. The apparatus of claim 1, wherein said frame comprises:
   two vertical side partitions;
   a main front panel pair attached to respective said vertical side partitions;
   a bottom panel attached to said vertical side partitions;
   a back panel attached to said vertical side partitions; and a second front panel disposed between said main front panel pair.

13. The apparatus of claim 12, wherein said second front panel further comprises a heat sink for said electrophoresis mold.

14. The apparatus of claim 12, wherein said back panel includes a plurality of holes which act as cooling vents for said electrophoresis apparatus.

15. The apparatus of claim 14, wherein the size of said holes is selected so as to prevent access of the experimenter to said second front panel, whereby the risk of electrical shock is reduced.

16. The apparatus of claim 12, further including clamping means disposed in said main front panel for physically contacting said electrophoresis mold on a side of said electrophoresis mold opposite to that of said second front panel.

17. The apparatus of claim 16, wherein each of said clamping means comprises:
post means attached to one of said main front panel pair, and
a clamping member movably disposed on said post means for rotation of said clamping member about said post means between
a first position in which said clamping member is not in front of said electrophoresis mold, which allows said electrophoresis mold to be removed from said frame, and
a second position in which said clamping member is in front of said electrophoresis mold, which acts to maintain said electrophoresis mold in said substantially vertical position.

18. The apparatus of claim 1, further including a top closure panel rotatably attached to said frame for substantially covering the top of said first buffer reservoir.

19. The apparatus of claim 1, further including a bottom closure panel rotatably attached to said frame for substantially covering the top of said lower buffer reservoir.

20. The apparatus of claim 18, wherein said top closure panel is adapted to move between open and closed positions,
said top closure panel when in the open position physically blocks an electrical connector which is in electrical contact with said first buffer solution, and
said top closure panel when in the closed position substantially covers the top of said first buffer solution.

21. The apparatus of claim 10, wherein said bottom closure panel is adapted to move between open and closed positions,
said bottom closure panel when in the open position physically blocks an electrical connector which is in electrical contact with said second buffer solution, and
said bottom closure panel when in the closed position substantially covers the top of said second buffer solution.

22. The apparatus of claim 1, wherein said first means for said first buffer reservoir comprises a flexible L-shaped mounting strip, and an electrode mounted thereon.

23. The apparatus of claim 1, wherein said first means for said second buffer reservoir comprises a flexible L-shaped mounting strip, and an electrode mounted thereon.

24. The apparatus of claim 22, wherein said electrode is made of platinum.

25. The apparatus of claim 23, wherein said electrode is made of platinum.

26. The apparatus of claim 1, further comprising upper buffer reservoir drain assembly means adapted to control drainage of said first buffer solution from said first buffer reservoir through said drainage pathway to said upper buffer reservoir drain container.

27. The apparatus of claim 25, wherein said upper buffer reservoir drain assembly means includes petcock means disposed in said frame.

28. The apparatus of claim 27, wherein said petcock means includes a drain hose clamp, and a knob threadably mounted on said drain hose clamp.

29. The apparatus of claim 28, wherein said drain hose clamp comprises an L-shaped clamp and a flat plate disposed thereon.

30. The apparatus of claim 1, wherein said first buffer reservoir has viewing means to allow an experimenter to view said first buffer solution contained in said first buffer reservoir.

31. The apparatus of claim 30, wherein said viewing means is a window.

32. The apparatus of claim 31, wherein said window is mounted in a hole in a wall of said first buffer reservoir.

33. The apparatus of claim 32, wherein said window is made of a substantially transparent material.

34. The apparatus of claim 1, wherein said frame includes at least one handle means adapted for carrying said vertical electrophoresis apparatus.

35. The apparatus of claim 34, wherein said handle means includes at least one hole formed in said frame.

36. The apparatus of claim 12, wherein at least one of said vertical side partitions includes a handle means.

* * * * *